United States Patent

Yamamoto et al.

[11] Patent Number: 5,991,030
[45] Date of Patent: Nov. 23, 1999

[54] APPARATUS FOR READING A LUMINESCENCE PATTERN OF A SAMPLE

[75] Inventors: Kenji Yamamoto; Hisanori Nasu; Toshimasa Watanabe; Yuuji Tsukamoto; Tateo Kondou; Takehiko Nishida; Hitoshi Fujimiya; Noriko Yurino, all of Yokohama, Japan

[73] Assignee: Hitachi Software Engineering Co., Ltd., Kanagawa-ken, Japan

[21] Appl. No.: 09/066,875

[22] Filed: Apr. 28, 1998

[30] Foreign Application Priority Data

Sep. 11, 1997 [JP] Japan ..................... 9-262953

[51] Int. Cl.⁶ ................. G01R 9/02; F21V 9/16
[52] U.S. Cl. ............. 356/346; 250/458.1; 250/459.1
[58] Field of Search ............ 356/346; 250/458.1, 250/459.1

[56] References Cited

U.S. PATENT DOCUMENTS 5,069,769  12/1991  Fujiyama et al.
5,736,410  4/1998   Zarling et al. ................. 356/346

FOREIGN PATENT DOCUMENTS 8-3481  1/1996  Japan.

OTHER PUBLICATIONS

Biotechniques, vol. 11, No. 1, 1991, "Improved Chemiluminescent DNA Sequencing", C. Martin et al, pp. 110–113.

*Primary Examiner*—Frank G. Font
*Assistant Examiner*—Roy M. Punnoose
*Attorney, Agent, or Firm*—Beall Law Offices

[57] ABSTRACT

The apparatus for reading a luminescence pattern is equipped with a stage on which the sample to be read is mounted. A photoreceptor disk is installed in the lower part of the stage and scans and condenses light from the luminescent pattern of the sample at positions determined by the rotation of a rotary plate. A transport mechanism causes the stage and the photoreceptor disk to undergo relative motion. An optical guide part guides the light from the luminescent pattern to a photoelectric converter. The optical guide part may include mirrors or one or more optical fibers. The photoelectric converter converts the light into an electrical signal. A controller controls how scanning is performed by the photoreceptor disk and transport mechanism and generates a read scanning position signal. A data processor performs data processing by converting the electrical signal into a digital signal and obtains a scanning position signal from the controller. Additionally, a laser light source may be used to shine laser light onto an electrophoresis gel of the sample.

27 Claims, 11 Drawing Sheets

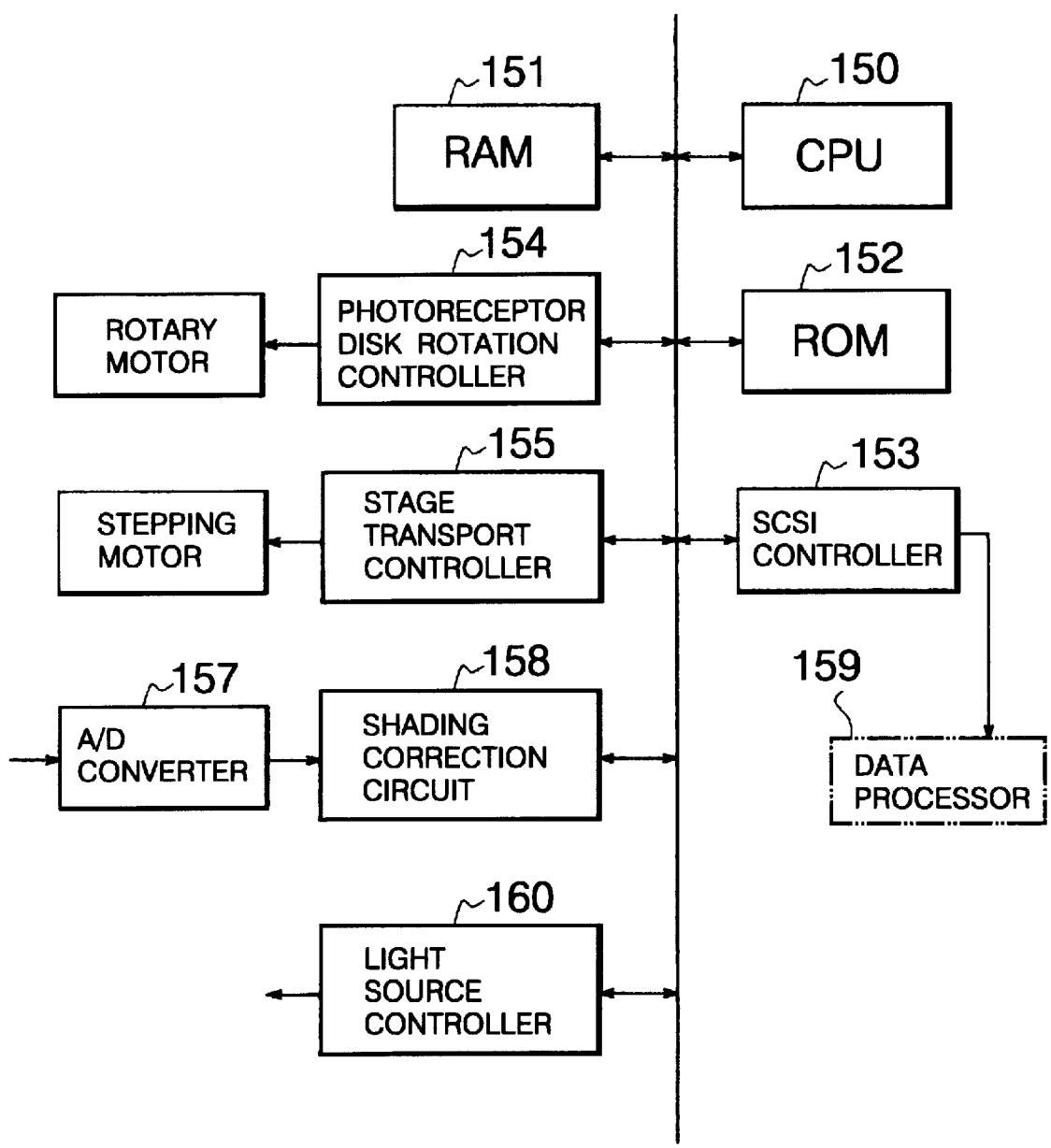

APPARATUS FOR READING A LUMINESCENCE PATTERN OF A SAMPLE

BACKGROUND OF THE INVENTION

The present invention relates to an apparatus for reading a luminescence pattern that scans a faint luminescence pattern emitted from a planar sample by scanning it with a rotary disk.

Gel electrophoresis analysis methods have hitherto been widely used for the differentiation and structural analysis of biological macromolecules such as proteins and nucleic acids. In the gel electrophoresis, they are analyzed by exploiting the principle that the migration distance of a sample in electrophoresis differs according to its molecular weight. This analysis method is appropriate for the analysis of minute sample quantities, and in general the sample amounts that can be obtained using gel electrophoresis are therefore often limited. In such cases there is a particular requirement for reliability and high sensitivity in the analysis process.

Reliability is an important concern when only a small amount of sample is available, and so electrophoresis patterns have hitherto been read by using a radioisotope to label the sample to be analyzed before it is injected into the gel where electrophoresis is performed, after which the gel is pasted to an X-ray film or the like which is thereby exposed, and this X-ray film is developed to bring out the pattern exposed by the radioisotope, which is then read.

However, radioisotopes are dangerous and must be handled with extreme care. In recent years, therefore, highly sensitive detection methods employing fluorescence and chemical luminescence (fluorescence method, chemiluminescence method) have been developed. These methods are also used in DNA base sequencing and in various types of tests such as southern plotting, western plotting and northern plotting.

The fluorescence method determines a sample's electrophoresis pattern by labeling the sample with a fluorescent substance and—once the electrophoresis has finished—irradiating laser light onto it and measuring the intensity distribution of fluorescent light emitted by this fluorescent substance. An example of apparatus for reading a fluorescence pattern is disclosed in Examined Japanese Patent Publication (JP-B) No.H8-3481 (or in the specification of U.S. Pat. No. 5,069,769).

Also, chemiluminescence reading methods that have hitherto been developed include the method described by C. Martin, L. Bresnick, R.-R. Juo, J. C. Voyta and I. Bronstein (Improved Chemiluminescent DNA Sequencing; Bio Techniques 8, pp. 110–113, 1991).

In the chemiluminescence method, the electrophoresis pattern is normally read in by hybridizing an enzyme that undergoes luminescence to a labeled probe or the like after electrophoresis has been completed, whereby the luminescence pattern of the sample to be analyzed is made to emit light in a particular way. The luminescence pattern of the luminescent sample is exposed to film for 10 to 30 minutes or thereabouts by bringing a fast film into close contact with a membrane from which the luminescent sample has been transferred, placing it inside a light-shielding case, and regulating the exposure time according to the luminescence.

It is noted that various types of fast film can be used here, such as the X-ray film used for radioisotopes. After the exposed film has been developed, it can be analyzed by visual pattern analysis or by various types of image processing software using image acquisition apparatus such as a camera or image scanner.

Incidentally, the abovementioned conventional luminescence pattern reading apparatus is dedicated to the analysis of samples by the fluorescence method, since reading luminescence patterns with the chemiluminescence method involves manual intervention, no dedicated reading apparatus has yet been specifically developed for reading luminescence with both the fluorescence method and the chemiluminescence method with a single reading apparatus.

Also, in the luminescence pattern reading apparatus of the chemiluminescence method, the light from a planar luminescence pattern that is faintly luminescent over its entire surface must be read before there is any change in the amount of luminescence. This necessitates the use of an optical sensor that is highly sensitive, in which case it is also necessary to have an optical system with a photoreceptor path and a scanning mechanism that condenses and inputs the faint light at the position of each pixel in the luminescence pattern.

To successively scan each individual pixel in the luminescence pattern while distinguishing their positions, it is necessary to have a mechanism that transports a photoreceptor window in two dimensions to positions corresponding to the pixels. To increase the speed at which the entire plane is scanned, the scanning window must be transported at high speed. With a conventional scanning mechanism where the scanning window is transported in straight lines and the sample has a width of, say, 200 mm, it is limited to about 3 reciprocating motions per second even if the mass of the condenser unit constituting the moving photoreceptor window is reduced to the bare minimum.

Incidentally, even if the transport speed at which the photoreceptor window scans the sample surface is increased, it does not necessarily mean that the reading speed of the overall apparatus can be increased without limit, as there is an upper limit determined by the relationship between the amount of light obtained from the position of each individual pixel in the luminescence pattern of the sample and the photosensitivity of the photosensor that is used.

If the condenser unit constituting the moving photoreceptor window is mechanically scanned at high speed (by a scanning mechanism), the photosensor (photoelectric conversion element) where the light from this condenser unit is introduced and detected has to detect amounts of light emitted very faintly such as fluorescence. Consequently, highly sensitive photosensors such as photomultipliers, cooled CCDs and image intensifiers, for example, are used. In this case, to ensure that the photosensor sensitivity remains stable, it is preferable to adopt a mechanical structure whereby the photosensor is attached at a static position rather than being mounted on a moving structure such as the carrier of the scanning mechanism. Furthermore, it is also preferable to be able to read the luminescence patterns of samples emitting different colors of light by discriminating between these colors.

SUMMARY OF THE INVENTION

It is also preferable that the reading apparatus is able to read the luminescence patterns of samples with high sensitivity using the analysis methods of both the fluorescence method and the chemiluminescence method.

The present invention solves the various problems of the prior art as mentioned above, and aims to provide an apparatus for reading a luminescence pattern which reads a luminescence pattern emitted faintly from a planar sample by using a rotary disk to scan it along arc-shaped paths.

Another aim of the present invention is to provide an apparatus for reading a luminescence pattern that is able to read luminescence patterns from samples using both the fluorescent and chemiluminescent analysis methods, and which reads a luminescence pattern emitted faintly from a planar sample by using a rotary disk to scan it along arc-shaped paths.

In order to attain the above objects, the present invention provides an apparatus for reading a luminescence pattern, capable of scanning and reading a luminescence pattern from a planar luminescent sample, comprising:

a stage on which the sample to be read is mounted;

a photoreceptor disk installed in the lower part of said stage, for scanning and condensing light from the luminescent pattern of the sample at positions determined by the rotation of said rotary plate;

a transport mechanism for causing said stage and said photoreceptor disk to undergo relative motion;

an optical guide part for guiding the light from the luminescent pattern, which has been condensed by said photoreceptor disk, to the photoreceptor entrance of a photoelectric converter;

a photoelectric converter for receiving the light guided out from said optical guide part, and converting it into an electrical signal;

a controller for controlling the scanning performed by said photoreceptor disk and said transport mechanism, and generating a read scanning position signal; and a data processor for performing data processing by converting the electrical signal from said photoelectric converter into a digital signal, and by obtaining a scanning position signal from said controller.

The present invention also provides an apparatus for reading a luminescence pattern, capable of scanning and reading a luminescence pattern from a sample, comprising:

a stage on which the sample to be read is mounted;

a photoreceptor disk composed of a rotary plate and installed in the lower part of said stage, for scanning and condensing light from the luminescent pattern of the sample at positions determined by the rotation of said rotary plate;

a transport mechanism for causing said stage and said photoreceptor disk to undergo relative motion;

an optical guide part for guiding the light from the luminescent pattern, which has been condensed by said photoreceptor disk, to the photoreceptor entrance of a photoelectric converter;

a dichroic mirror provided in the optical path of said optical guide part;

an excitation light source for emitting excitation light which is introduced via said dichroic mirror and excites a fluorescent substance in the sample to be read;

a photoelectric converter for receiving the light guided out from said optical guide part, and converting it into an electrical signal;

a controller for controlling the scanning performed by said photoreceptor disk and said transport mechanism, and generating a read scanning position signal; and a data processor for performing data processing by converting the electrical signal from said photoelectric converter into a digital signal and obtaining a scanning position signal from said controller.

In another aspect, the present invention provides an apparatus for reading a luminescence pattern, wherein said data processor is equipped with an image memory for storing the luminescence pattern, and is equipped with a data processing unit for transforming the polar coordinates scanned by said photoreceptor disk into rectangular coordinates.

In another aspect, the present invention provides an apparatus for reading a luminescence pattern, wherein said photoreceptor disk is equipped with a condenser unit including lenses, a wavelength-selective filter and a pinhole; and wherein the pinhole of said condenser unit is provided in said photoreceptor disk.

In another aspect, the present invention provides an apparatus for reading a luminescence pattern, wherein said optical guide part is an optical fiber whose light-entrance end is connected to the condenser unit of said photoreceptor disk, and whose light-exiting end is provided at the center of rotation of said photoreceptor disk, in one embodiment; and wherein said optical guide part is an optical path whose light-entrance end is a first mirror disposed in the condenser part of said photoreceptor disk, and whose light-exiting end is a second mirror disposed so as to be at the center of rotation of said photoreceptor disk, in another embodiment.

In another aspect, the present invention provides an apparatus for reading a luminescence pattern, wherein said photoelectric converter is a photomutiplier and is installed at the center of rotation of said photoreceptor disk; and wherein the condenser unit provided on said photoreceptor disk is provided adjoining said stage.

In another aspect, the present invention provides an apparatus for reading a luminescence pattern, wherein said photoreceptor disk is equipped with a plurality of condenser units including lenses, wavelength-selective filters and pinholes, and the wavelength-selective filters of the plurality of condenser units each have different selection wavelengths, in order to read a multi-color luminescence pattern.

In another aspect, the present invention provides an apparatus for reading a luminescence pattern, wherein the dichroic mirror is provided at the light-exiting end of said optical guide part and at the center of rotation of said photoreceptor disk, and wherein the excitation light of said excitation light source is produced using a laser light source with expanded beam width, in order to read a liminescence pattern using the analysis method of the fluorescence method.

In another aspect, the present invention provides an apparatus for reading a luminescence pattern, wherein said photoreceptor disk is equipped with a plurality of condenser units including lenses, wavelength-selective filters and pinholes, and the wavelength-selective filters of the plurality of condenser units each have different selection wavelengths, the dichroic mirror is provided at the light-exiting end of said optical guide part and at the center of rotation of said photoreceptor disk, and the excitation light of said excitation light source is produced using a laser light source with expanded beam width in the range in which the object to be scanned is read with respect to the dichroic mirror, in order to read a multi-color luminescence pattern using the analysis method of the fluorescence method.

When reading a luminescence pattern by scanning a planar luminescent sample with apparatus for reading a luminescence pattern according to the present invention having these various characteristics, the sample to be read is mounted on the stage, and reading of the luminescence pattern is started. As the reading begins, the photoreceptor disk installed at the lower part of this stage is rotated, and the light from the sample's luminescence pattern is condensed by scanning its photoreception position according to the rotation of the rotating plate. Here, the mechanical driving of the photoreceptor disk and the stage is controlled by the transport mechanism; that is, it is controlled so as to create relative motion between the stage and the photoreceptor disk. Then, the light of the luminescence pattern condensed by the photoreceptor disk is guided out to the photoreceptor entrance of the photoelectric converter by guiding it with the optical guide part. The photoelectric converter receives the optical signal from the optical guide part and converts it into an electrical signal which it supplies to the data processor.

In this case, since the controller controls how the scanning is performed by the photoreceptor disk and the transport mechanism and generates a read scanning position signal, the data processor converts the electrical signal from the photoelectric converter into a digital signal, and performs data processing by obtaining the scanning position signal from the controller.

The data processor is equipped with the data processing unit and the image memory, and when a luminescence pattern is stored in the image memory, the data processing unit receives the scanning position signal from the controller, and uses this scanning position signal to convert the polar coordinate system of the photoreceptor disk into a rectangular coordinate system. In this way, it is possible to obtain a luminescence pattern no different from that obtained when scanning with a straight-line scanning mechanism.

When using the fluorescent analysis method to read a luminescence pattern from a sample, the fluorescent material in the sample is excited by an excitation light source. Consequently, the scanning of the excitation light over the sample and the scanning of the luminescence pattern from the sample are performed simultaneously. As in the scanning of a luminescence pattern with the chemiluminescence method mentioned above, the sample to be read is mounted on the stage, and reading of the luminescence pattern is started. As the reading begins, the excitation light emitted by the excitation light source is guided by the optical guide part through the dichroic mirror provided in the optical path, and the luminescence pattern thereby emitted from the sample is detected.

In this case, the photoreceptor disk installed in the lower part of the stage scans and condenses the light emitted from the photoreception position of the sample's luminescence pattern with the rotating plate. The mechanical driving of the photoreceptor disk and the stage is controlled by the transport mechanism. That is, it is controlled so as to create relative motion between the stage and the photoreceptor disk. The light of the luminescence pattern condensed by the photoreceptor disk is guided out to the photoreceptor entrance of the photoelectric converter by guiding it with an optical guide part. The photoelectric converter receives the optical signal from the optical guide part and converts it into an electrical signal which it supplies to the data processor.

BRIEF DESCRIPTION OF THE DRAWINGS

FIG. 3a is a plan view of the photoreceptor disk, and FIG. 3b is a side view in partial cross section.

FIG. 8a is a plan view of the photoreceptor disk, and FIG. 8b is a side view in partial cross section.

FIG. 9 is a block diagram illustrating the electrical system of the apparatus for reading a luminescence pattern according to the second embodiment.

DESCRIPTION OF PREFERRED EMBODIMENTS

Specific modes of implementing the present invention will be described by way of the following embodiments.

Figure 1:
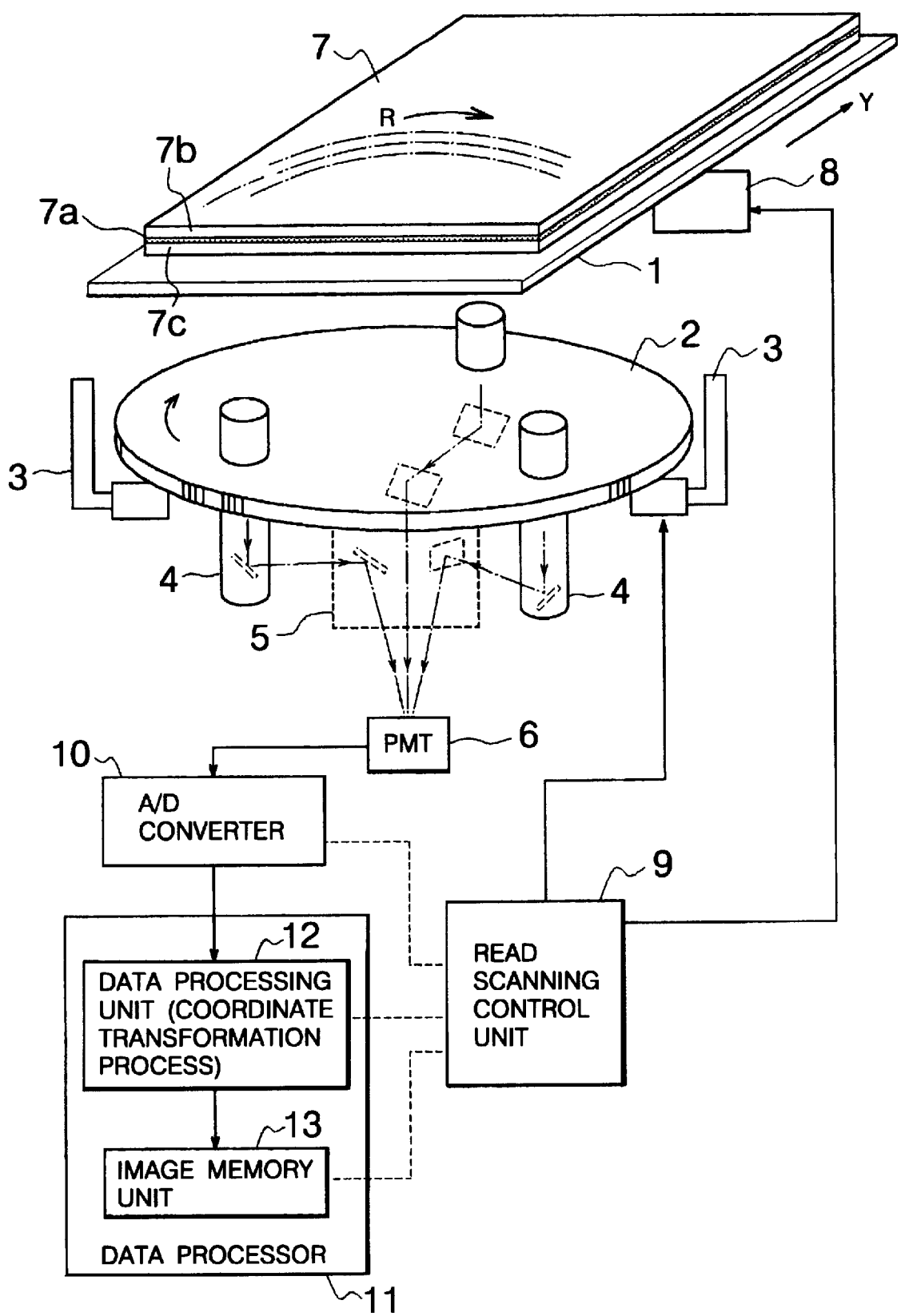
FIG. 1 illustrates an apparatus for reading a luminescence pattern according to the first embodiment of the present invention.

FIG. 1 illustrates the configuration of the apparatus for reading a luminescence pattern relating to a first embodiment of the present invention. In FIG. 1, item 1 is a stage on which the sample is placed, item 2 is a photoreceptor disk, item 3 is a rotary motor including a support for the photoreceptor disk, item 4 is a condenser unit, item 5 is an optical guide part, item 6 is a photomultiplier of the photoelectric converter, item 7 is an electrophoresis gel of the sample to be read, item 8 is a transport mechanism that transports the stage, item 9 is a read scanning control unit, item 10 is an analog-to-digital (A/D) converter, item 11 is a data processor, item 12 is a data processing unit which performs a coordinate transformation process, and item 13 is an image memory unit.

The operation of the apparatus for reading a luminescence pattern having this sort of configuration is summarized in the following. When scanning and reading the luminescence pattern of a planar luminescent sample which is made, for example, by labeling DNA with a luminescent substrate, dipping the gel that has been subjected to electrophoresis in a luminescent liquid, and reading the luminescence pattern of the gel that has been made chemiluminescent, the electrophoresis gel 7 that is to be read is mounted on the stage 1, and the apparatus is instructed to read the luminescence pattern. Here, the electrophoresis gel 7 that is to be read consists of a polyacrylamide gel 7a sandwiched between the glass supporting plates 7b and 7c.

Readings can also be made by hybridizing the sample with a probe labeled with a luminescent substrate in a biochip (the chambers of a minute chip partitioned into a plurality of boxes, in which the probe, the sample and the like are reacted together), thereby allowing the target DNA to be detected from the resulting luminescence pattern, in which case the biochip that is to be read is mounted on the stage 1 in the same way as in the case of a gel, and the apparatus is instructed to read the luminescence pattern.

In the description of this embodiment, the case where the electrophoresis gel 7 is read will be described. The electrophoresis gel 7 of the sample to be read is mounted on the stage 1, and an instruction to begin the reading operation is issued from a console panel (not illustrated), whereupon a start signal for controlling the luminescence pattern reading is output, the read scanning control unit 9 controls the transport mechanism 8 and the rotary motor 3, and the reading scan begins. In the reading scan, the secondary scanning in the Y direction is performed by the transport mechanism 8, which transports the stage 1 in a straight line in the Y direction, and the primary scanning in the X direction is performed by the rotary motor 3 turning the photoreceptor disk 2, whereby the condenser unit 4 provided on this photoreceptor disk 2 moves rotationally over the arc-shaped scan lines.

That is, the photoreceptor disk 2 installed in the lower part of the stage 1 rotates, and according to the rotational motion of the condenser unit 4 provided on this photoreceptor disk 2, the photoreception position of the light from the reading surface of the luminescence pattern of the electrophoresis gel 7 of the sample is scanned by the rotating plate, and the light of the luminescence pattern is condensed. In this case, the read scanning control unit 9 controls the rotary motor 3 and the transport mechanism 8 controls the read scanning position by driving the photoreceptor disk 2 and the stage 1, at which time, the reading position at which the condenser unit 4 condenses the light from the reading surface of the luminescence pattern, is generated as a read scanning position signal in polar coordinates by the read scanning control unit 9 according to the control of the rotary motor 3 and the transport mechanism 8. Accordingly, in data processor 11, data processing unit 12 uses this read scanning position signal to store the corresponding position in the image memory 13.

Also, in this case, when recording a digital signal of the luminescence pattern at positions in the image memory corresponding to the positions of pixels in the read luminescence pattern, the data processing unit 12 which performs a coordinate transformation process in the data processor 11 transforms the positions of the arc-shaped scan lines of the photoreceptor disk 2 into a coordinate system of rectangular coordinates.

In this way, due to the relative motion of the stage 1 and the photoreceptor disk 2 and the rotation of the photoreceptor disk 2, the condenser unit 4—which constitutes a photoreceptor window—scans and reads the luminescence pattern by moving along an arc-shaped path. At this time, the light of the luminescence pattern condensed by the condenser unit 4 of the photoreceptor disk 2 is, as mentioned below, guided by the optical guide part 5 configured from a combination of a plurality of mirrors, and introduced into the photoreceptor entrance of the photomultiplier 6 of the photoelectric converter 10. Here, the photomultiplier 6 receives light from the luminescence pattern guided by the optical guide part 5, transforms it into an electrical signal, converts it into a digital signal with the analog-to-digital (A/D) converter 10, and supplies it to the data processor 11.

As mentioned above, the data processor 11 is equipped with the data processing unit 12 which performs a coordinate transformation process and the image memory 13, and when the luminescence pattern is stored in the image memory 13, the data processing unit 12 obtains the scanning position signal from the controller, and from this scanning position signal it converts the polar coordinate system of the positions scanned by the photoreceptor disk 2 into a rectangular coordinate system and stores them in the image memory 13. In this way it is possible to obtain a luminescence pattern no different from that obtained by scanning with a straight-line scanning mechanism.

Figure 2:
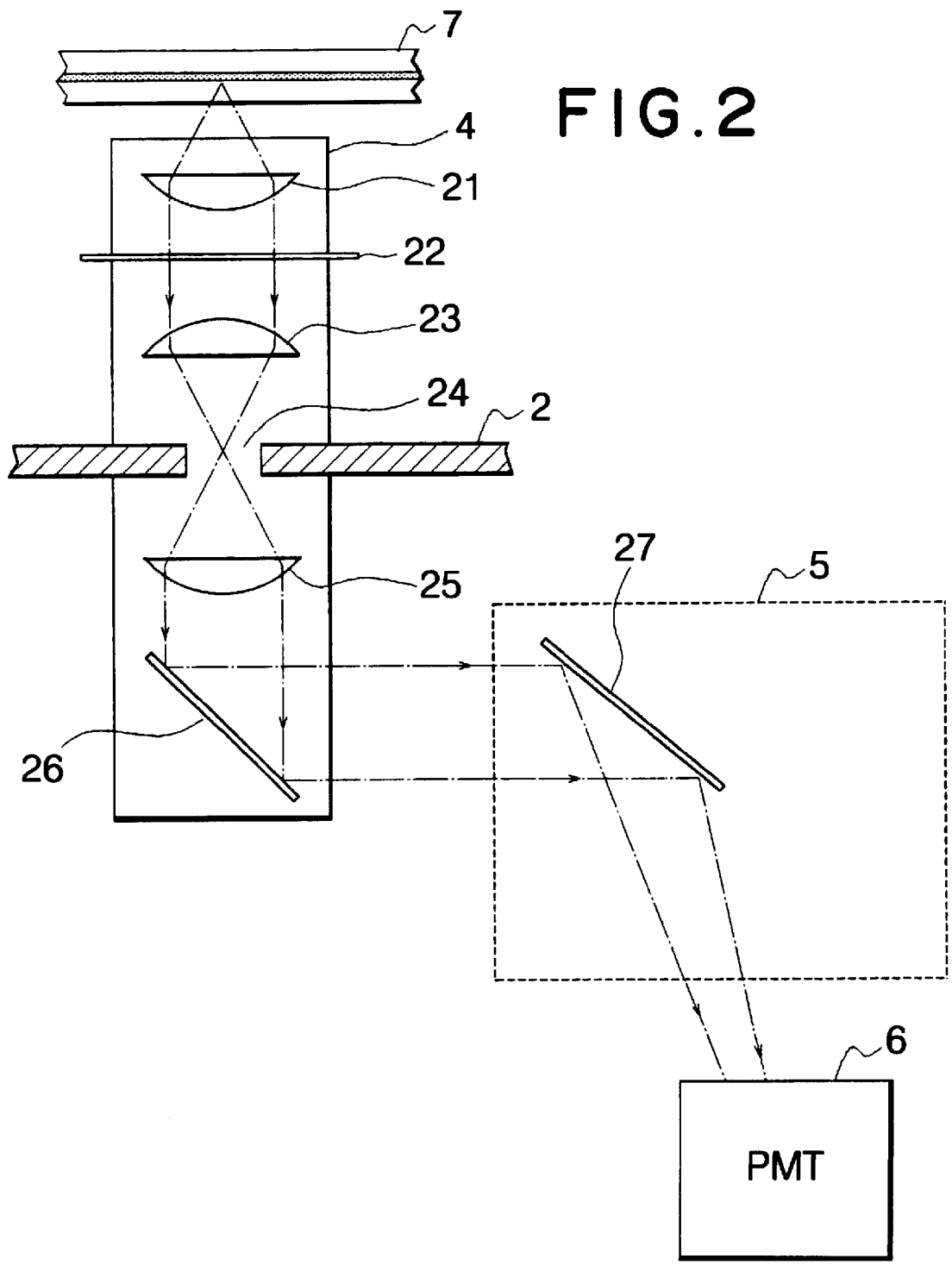
FIG. 2 illustrates the optical path for photoreception of the luminescence pattern with a condenser unit and an optical guide part according to the first embodiment of the present invention.

FIG. 2 illustrates the optical path whereby the luminescence pattern is detected with a condenser unit and an optical guide part. In FIG. 2, item 2 is a photoreceptor disk, item 4 is a condenser unit, item 5 is an optical guide part, item 6 is a photomultiplier, item 7 is an electrophoresis gel of the sample to be read, item 21 is a first lens, item 22 is a wavelength-selective filter, item 23 is a second lens, item 24 is a pinhole, item 25 is a third lens, item 26 is a first planar mirror, and item 27 is a second planar mirror.

The operation will be described in the following with reference to FIG. 2. The light emitted from the electrophoresis gel 7 of the sample persists for at least 10 or 20 minutes because it is produced by chemiluminescence, and so the luminescence pattern emitted from the sample is scanned and read in during this period and stored in corresponding positions in the image memory. This read scanning is performed by making a plurality of scans over the entire luminescence pattern, during which the amounts of light in each pixel of the luminescence pattern are accumulated. That is, once a single scan over the entire luminescence pattern has been completed, the stage 1 is returned to its starting position, and the read scanning control unit 9 controls the rotary motor 3 and the transport mechanism 8 so as to perform the scan again. These operations are performed repeatedly. As a result, the amounts of light in each pixel of the entire luminescence pattern are accumulated together, and an image is built up in the pixels corresponding to the luminescence pattern.

As shown in FIG. 2, the condenser unit 4 uses a hole part provided in the photoreceptor disk 2 as a pinhole, and is provided with a housing part in which the lenses and the like are provided across both sides of the rotating plate. The lens of the photoreceptor part is installed below the electrophoresis gel 7 of the luminescent sample sandwiched between the glass plates so as to be situated close to it. The optical system of the condenser unit 4 consists of the first lens 21, the wavelength-selective filter 22, the second lens 23, the pinhole 24 which is the hole part provided in the rotary disk 2, and the third lens 25, and the optical system of the optical guide part 5 consists of the first planar mirror 26 and the second planar mirror 27.

Once the light emitted from the electrophoresis gel 7 of the sample has been collimated by passing through the first lens 21 of the condenser unit 4, the target wavelength is selected by passing through the wavelength-selective filter 22. The light is then condensed by the second lens 23, and the background noise component of the received optical components is eliminated by passing through the pinhole 24, which is the hole part in the photoreceptor disk 2 disposed at the focal point of the second lens 23. That is, the light that has passed through the pinhole 24 corresponds only to the light from a single point on the sample (electrophoresis gel 7). This light is collimated again by the third lens 25 and redirected by the first planar mirror 26 and the second planar mirror 27 to guide its optical path toward the photomultiplier 6, where it is sensed.

Figure 3A:
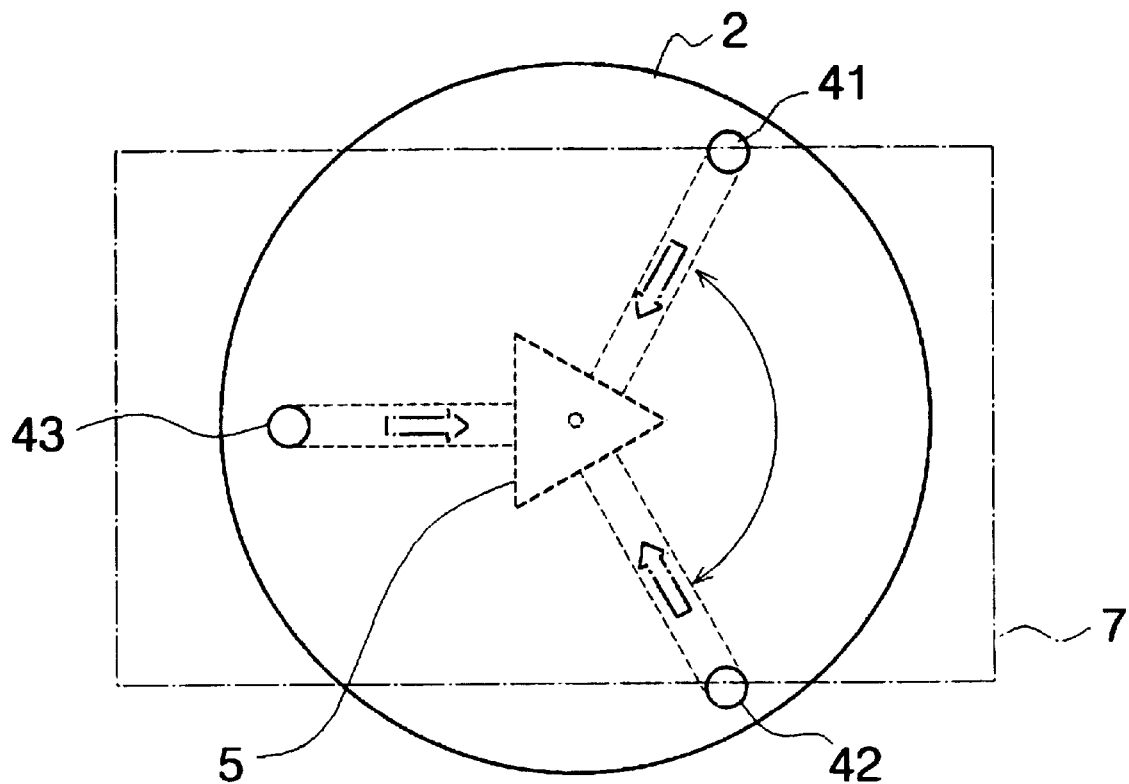
FIGS. 3a and 3b illustrate the positional relationship of the plurality of condenser units provided in a photo-receptor disk configured so as to read a multicolored luminescence pattern in the apparatus for reading a luminescence pattern according to the first embodiment of the present invention.
Figure 3B:
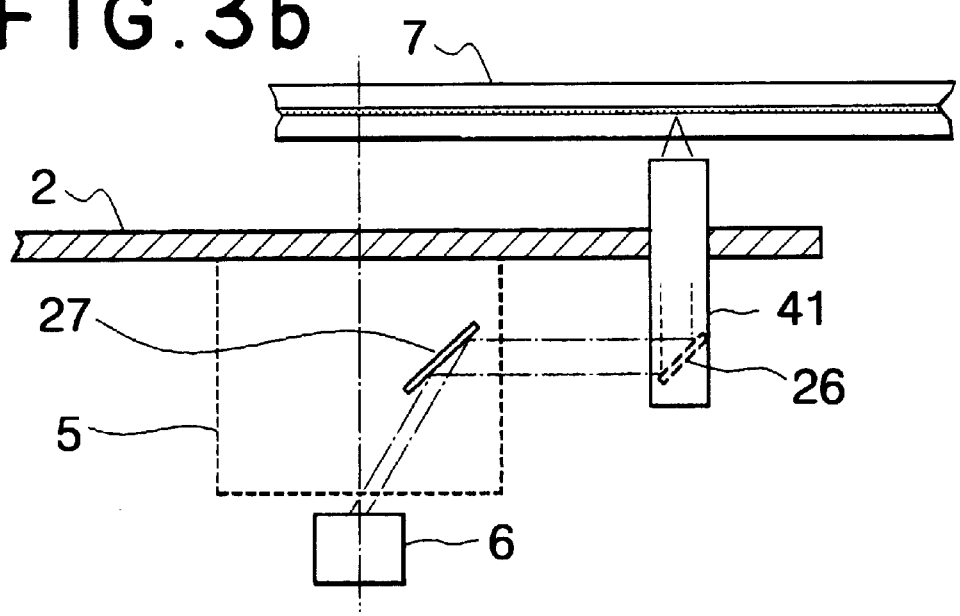

FIGS. 3a and 3b illustrate the positional relationship of the plurality of condenser units provided on the photoreceptor disk configured so as to read a multi-color luminescence pattern; FIG. 3a is a plan view of the photoreceptor disk and FIG. 3b is a side view in partial cross section.

As shown in FIG. 3a, three condenser units 41, 42 and 43 are provided on the photoreceptor disk 2 at positions on the circumference of the same circle and separated from each other by rotational angles of 120 degrees. These three condenser units 41, 42 and 43 each have the same configuration of a pinhole, lenses and the like, but their wavelength-selective filters 22 each have different selection wavelengths, and they are configured to selectively receive light of different colors. In this way, they can scan each color of a multi-color luminescence pattern by condensing light of different colors from the luminescence pattern along the same arc-shaped scan lines.

The optical guide part 5 is provided at the rotational center position of the photoreceptor disk 2, and the light of the luminescence pattern that has been condensed by the lenses and pinholes of each condenser unit 41, 42 and 43 is sent toward the optical guide part 5 provided at the rotational center position of the photoreceptor disk 2 by a planar mirror 26 provided in the lower part of each condenser unit.

As shown in FIG. 3b, the optical guide part 5 is provided with the planar mirrors 27 so that it can redirect the light sent in from each of the condenser units 41, 42 and 43 toward the photomultiplier 6. That is, the planar mirrors 27 are fixed back-to-back opposite each of the condenser units 41, 42 and 43 to form a triangular shape. This optical guide part 5 is fixed to the photoreceptor disk 2 and rotates in unison with the photoreceptor disk 2, and outputs the light from the condenser units 41, 42 and 43 to the photomultiplier 6, which is fixed to the housing of the luminescence pattern reading apparatus (not illustrated) and does not rotate. This photomultiplier 6 is provided at the center of rotation of the photoreceptor disk 2, and its relative positional relationship to the optical guide part 5 does not change. It is noted that a configuration is adopted in which a shutter mechanism (not illustrated) is provided in the optical paths of each of the condenser units, so that when the condenser unit 41 is positioned at the scan line that is currently being read, the light from the condenser units (42 and 43) that are not positioned at a read scanning line does not arrive at the photoreceptor entrance of the photomultiplier 6. Specifically, the shutter mechanism is provided with, for example, a mask that covers two thirds of the optical guide part 5 on the left-hand side that is not related to the region over which the reading scan lines move. It is also configured so that the photoreceptor entrance of the photomultiplier 6 is provided slightly shifted from the center of rotation, so that only light from the condenser unit in the region over which the reading scan lines move is guided to the photoreceptor entrance.

With such a configuration, the gel 7a of the sample is sandwiched between the glass supporting plates 7b and 7c, and light from the luminescence pattern of the electrophoresis gel 7 of said luminescent sample at the respective positions of the condenser units 41, 42 and 43 provided on the rotating photoreceptor disk 2 is condensed and sent to the optical guide part 5, whereupon, while the photoreceptor disk 2 and the optical guide part 5 rotate, the light from the condenser units 41, 42 and 43 is sent out to the same position at the photoreceptor entrance of the fixed photomultiplier 6. The photomultiplier 6 outputs an electrical signal according to the amount of light condensed from the photoreceptor entrance.

Figure 4:
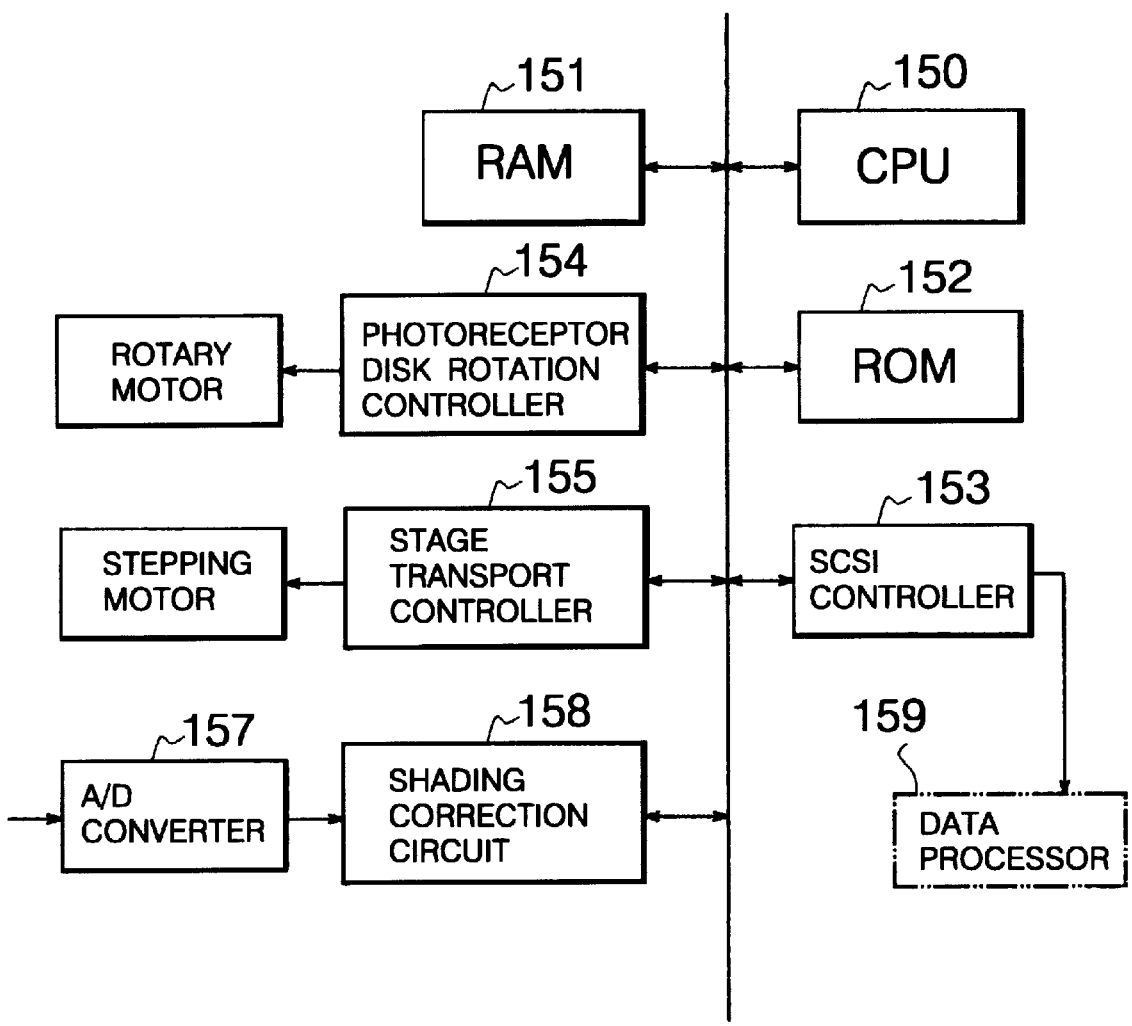
FIG. 4 is a block diagram illustrating the configuration of the electrical system of the apparatus for reading a luminescence pattern according to the first embodiment.

FIG. 4 is a block diagram showing the configuration of the electrical system of the luminescence pattern reading apparatus. As shown in FIG. 4, the configuration of the electrical system comprises, a microprocessor (CPU) 150 for executing the control processing of the luminescence pattern reading apparatus, a read-only memory (ROM) 152 for storing the control software program, a random access memory (RAM) 151 which provides a memory area for temporary data storage, an area used for image memory, and a memory area for other forms of data processing, a photoreceptor disk rotation controller 154, a stage transport controller 155, an A/D converter 157 for analog-to-digital conversion of the analog signal made by converting the received light into an electrical signal into digital data, a shading correction circuit 158 for correcting the fixed offset in the optical measurement system of the photoreceptor paths of the condenser units, and a SCSI controller 153 which controls the interface with an external data processor 159.

The overall electrical system operates as follows: as the power source is connected, each part of the apparatus is first initialized, and when the initialization process has finished, the reading of the sample's luminescence pattern is controlled. Here, details of the initialization process might include processes such as, for example, checking read-only memory (ROM) 152 and random access memory (RAM) 151, checking the rotary operation of the photoreceptor disk, checking the stage transport operation, and initializing the interface unit of the SCSI controller that controls the interface.

On completing the initialization process, the system stands by for a command from the host (data processor 159). When a reading command signal or the like has arrived, this command is processed and it once again returns to the command standby mode. Here, the operations to control the luminescence pattern reading are explained in the description of FIG. 1 above.

Figure 5:
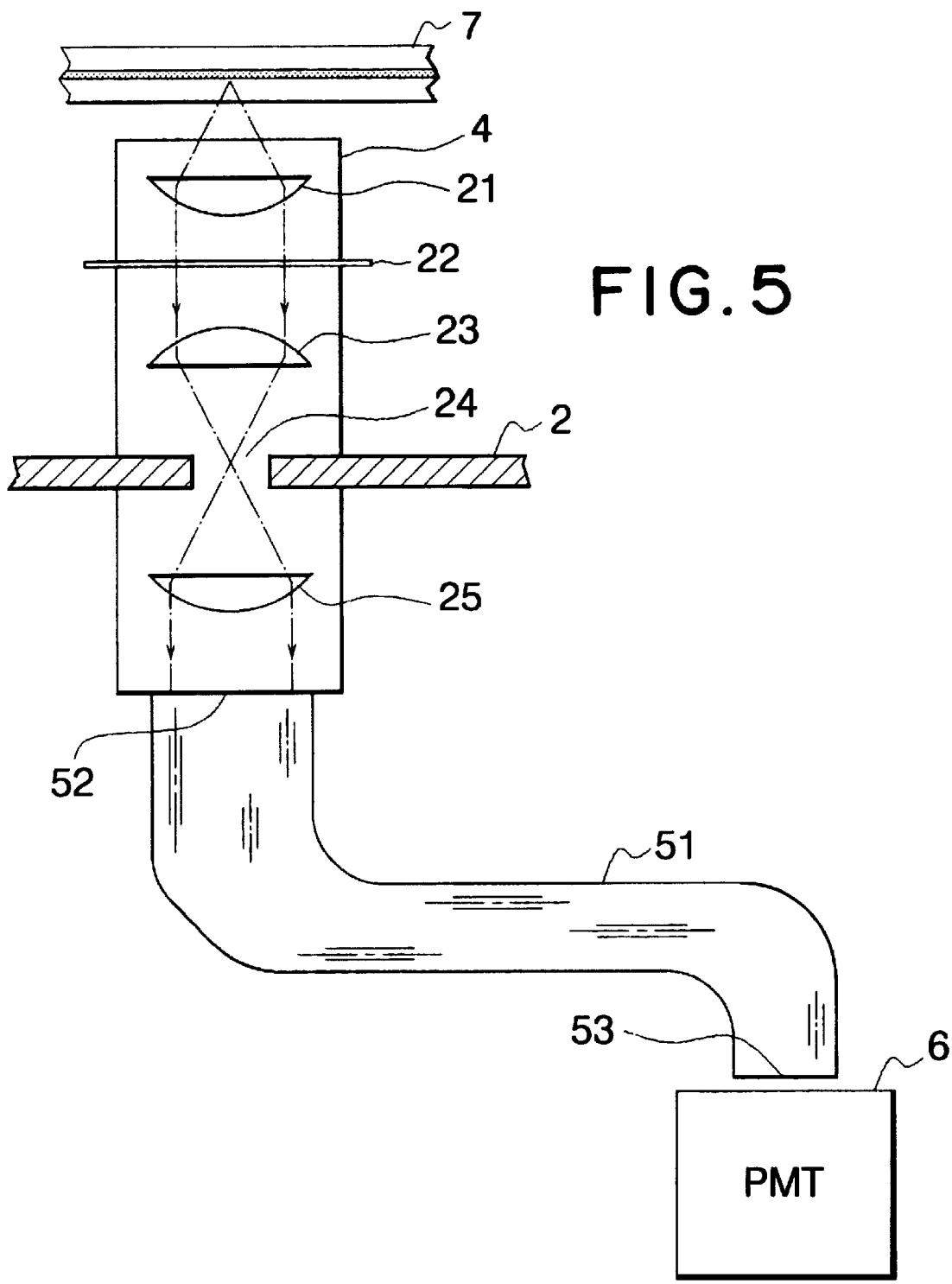
FIG. 5 illustrates a variant example in which the optical guide part in the first embodiment of the present invention is configured from an optical fiber.

Next, a variant embodiment of the luminescence pattern reading apparatus according to the first embodiment of the present invention is described. FIG. 5 describes a variant wherein the optical guide part is configured from an optical fiber. The function of the optical guide part is to send light from the condenser unit to the photo-multiplier, and so instead of the configuration of two planar mirrors in the abovementioned embodiment it can be configured to use an optical fiber to guide the condensed light directly to the photomultiplier.

That is, in this variant configuration as shown in FIG. 5, an optical fiber 51 is disposed with its light-entrance end 52 at the light-exiting end from the lens 25 of the condenser unit 4, and with its light-exiting end 53 disposed at the photoreceptor entrance of the photomultiplier 6. As in the abovementioned embodiment, the optical fiber 51 of the optical guide part is fixed to the photoreceptor disk 2, and rotates together with the photoreceptor disk 2. The light-exiting end of the optical fiber 51 is disposed so as to be positioned on the axis of the photoreceptor disk 2 at the rotational center thereof. The light-exiting ending from the fiber thereby reaches the photoreceptor entrance of the fixed photomultiplier 6. When this configuration is adapted for multi-color operation, a structure is adopted wherein a plurality of condenser units are provided, and the light-exiting ends of the plurality of optical fibers leading away from these condenser units are brought together at the position of the photoreceptor entrance of the photomultiplier 6.

Figure 6:
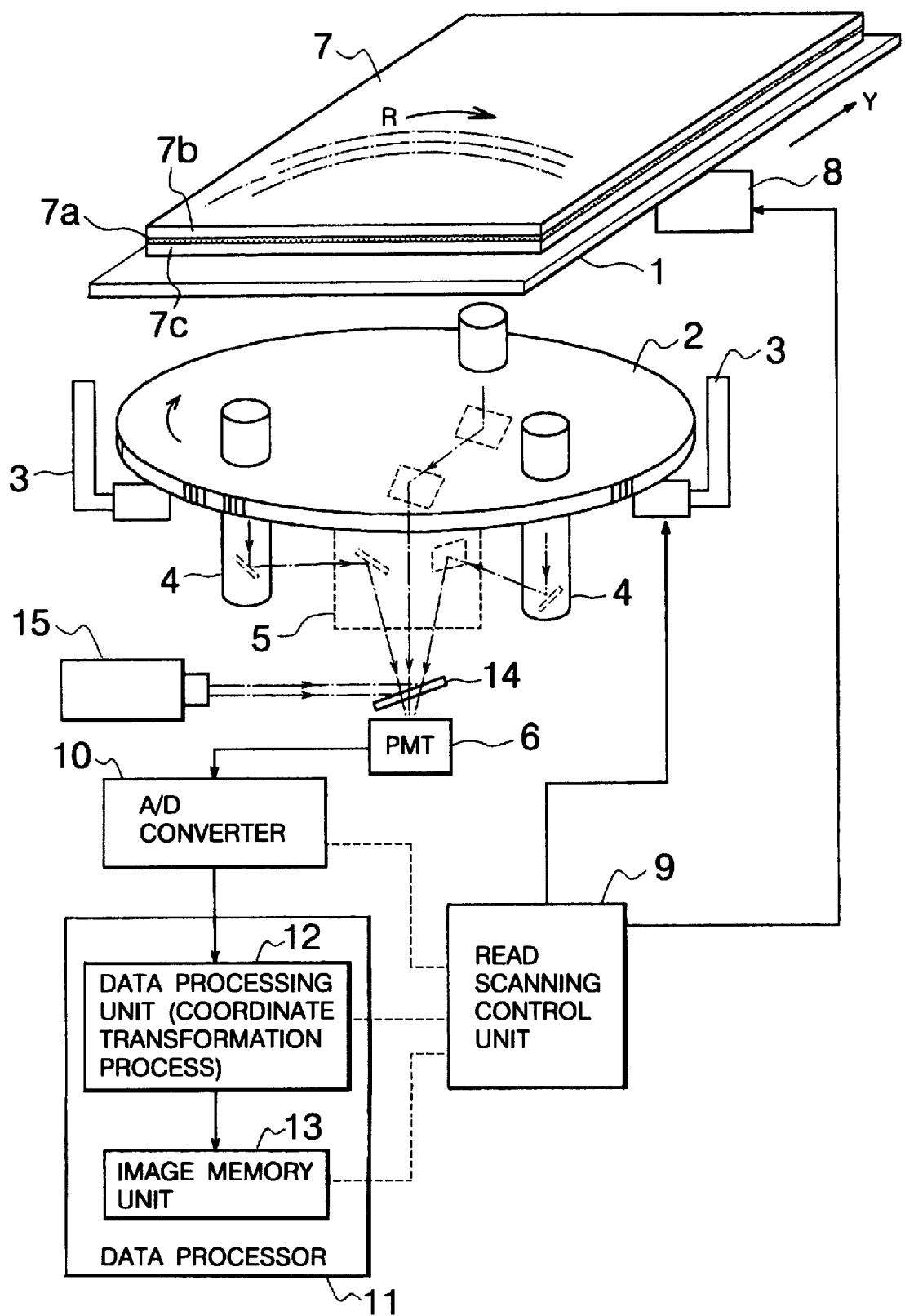
FIG. 6 illustrates an apparatus for reading a luminescence pattern according to a second embodiment of the present invention.

FIG. 6 illustrates the configuration of the apparatus for reading a luminescence pattern relating to a second embodiment of the present invention. In FIG. 6, item 1 is a stage on which the sample is placed, item 2 is a photoreceptor disk, item 3 is a rotary motor including a support for the photoreceptor disk, item 4 is a condenser unit, item 5 is an optical guide part, item 6 is a photomultiplier of the photoelectric converter, item 7 is an electrophoresis gel of the sample to be read, item 8 is a transport mechanism that transports the stage, item 9 is a read scanning control unit, item 10 is an analog-to-digital (A/D) converter, item 11 is a data processor, item 12 is a data processing unit which performs a coordinate transformation process, item 13 is an image memory unit, item 14 is a dichroic mirror, and item 15 is a laser light source.

Of these elements, those that are the same as the elements of the first embodiment described in FIG. 1 are denoted with the same reference numerals. In the apparatus for reading a luminescence pattern according to the second embodiment, the laser light source 15 and the dichroic mirror 14 are provided as elements for shining laser light onto the electrophoresis gel of a sample tagged with a fluorescent substrate.

The action of apparatus for reading a luminescence pattern according to the second embodiment having this sort of configuration is summarized in the following. In the apparatus for reading a luminescence pattern according to the second embodiment, excitation light is irradiated onto the electrophoresis gel of a sample labeled with a fluorescent substrate, whereby the fluorescent substrate in the sample emits light by fluorescence, which is then read. For this purpose, the reading is done by introducing excitation light from the laser light source 15 into the optical path via the dichroic mirror 14. As in the case mentioned earlier, the electrophoresis gel 7 that is to be read is mounted on the stage 1, and the apparatus is instructed to read the luminescence pattern. Here, the electrophoresis gel 7 that is to be read consists of a polyacrylamide gel 7a sandwiched between glass supporting plates 7b and 7c. Readings are also made in the same way when a biochip is used for the sample.

The electrophoresis gel 7 of the sample to be read is mounted on the stage 1, and an instruction to begin the reading operation is issued from a console panel (not illustrated), whereupon a start signal for controlling the luminescence pattern reading is output, the read scanning control unit 9 controls the transport mechanism 8 and the rotary motor 3, and the reading scan begins. At this time, the laser light source 15 is turned on and emits excitation light. The excitation light has a relatively large beam width, and excitation light with a large beam width is irradiated over the entire surface of the dichroic mirror 14. The excitation light is reflected by the dichroic mirror 14, passes through the optical guide part 5 and the condenser unit 4, and irradiates on the part of the electrophoresis gel 7 that is being read. In the reading scan, the secondary scanning in the Y direction is performed by the transport mechanism 8, which transports the stage 1 in a straight line in the Y direction, and the primary scanning in the X direction is performed by the rotary motor 3 turning the photoreceptor disk 2, whereby the condenser unit 4 provided on this photoreceptor disk 2 moves rotationally over the arc-shaped scan lines.

The read scanning is done in the same way as with the first embodiment mentioned above, but in this apparatus for reading a luminescence pattern according to the second embodiment, the excitation light for exciting the luminescent substrate in the sample is emitted from laser light source 15, this light is reflected by the dichroic mirror 14, and the reflected light passes through the optical guide part 5, through the lenses of the condenser unit 4 provided in the photoreceptor disk 2, and irradiates from below onto the part of the sample electrophoresis gel 7 that is to be read. Accordingly, this excitation light is scanned over the electrophoresis gel 7 of the sample in conjunction with the rotation of the photoreceptor disk 2.

The photoreceptor disk 2 is installed in the lower part of the stage 1, and the rotation of this photoreceptor disk 2 causes the condenser unit 4 provided on the photoreceptor disk 2 to move rotationally, whereby the photoreception position of the light from the reading surface of the electrophoresis gel 7 of the sample is scanned along arc-shaped lines. While this scanning takes place, the fluorescent emitted light is condensed. In this case, the read scanning control unit 9 controlling the the rotary motor 3 and the transport mechanism 8 controls the read scanning position by driving the photoreceptor disk 2 and the stage 1, at which time the reading position at which the condenser unit 4 condenses the light from the reading surface of the electrophoresis gel 7, which emits fluorescent light, is generated as a read scanning position signal in polar coordinates by the read scanning control unit 9 according to the control of the rotary motor 3 and the transport mechanism 8. Accordingly, in the data processor 11, the data processing unit 12 uses this read scanning position signal to store the corresponding position in the image memory 13.

Also, in this case, when recording a digital signal of the fluorescent light pattern at positions in the image memory corresponding to the positions of pixels in the read fluorescent light pattern, the data processing unit 12 which performs a coordinate transformation process in the data processor 11 transforms the positions of the arc-shaped scan lines of the photoreceptor disk 2 into a coordinate system of rectangular coordinates.

In this way, due to the relative motion of the stage 1 and the photoreceptor disk 2 and the rotation of the photoreceptor disk 2, the condenser unit 4—which constitutes the photoreceptor window—irradiates the excitation light onto the sample, and scans and reads the fluorescent light pattern by moving along an arc-shaped path. At this time, the light of the fluorescent light pattern condensed by the condenser unit 4 of the photoreceptor disk 2 is guided by the optical guide part 5 and reaches the dichroic mirror 14. At the dichroic mirror 14, the light from the fluorescent light pattern is allowed to pass straight through, and so this light is introduced into the photoreceptor entrance of the photomultiplier 6 of the photoelectric converter. The photomultiplier 6 receives the light from the fluorescent light pattern that has been introduced into the photoreceptor entrance thereof, and transforms it into an electrical signal. This is then converted into a digital signal by the analog-to-digital (A/D) converter 10, and supplied to the data processor 11.

That is, the apparatus for reading a luminescence pattern according to the second embodiment differs from the above-mentioned first embodiment in that, when reading the electrophoresis gel 7 of a sample labeled with a fluorescent substrate, the laser light source 15 is turned on to make it emit laser light, which is used as excitation light by introducing it into the optical path via the dichroic mirror 14 to make it irradiate on the part of the electrophoresis gel 7 of the sample that is being read. The light emitted from the laser light source 15 is introduced into the optical path by reflecting it with the dichroic mirror 14, passes through the optical guide part 5, and is guided to the part of the electrophoresis gel 7 of the sample that is being read.

The fluorescent light emitted from the sample that has been excited by the excitation light from the laser light source 15 is dealt with in the same way as in the luminescent pattern reading of the first embodiment mentioned above; that is, it passes through the optical guide part 5, is introduced into the photomultiplier via the dichroic mirror 14, and is finally subjected to suitable processing in the data processor. The dichroic mirror 14 used here is one that reflects light at the wavelength emitted from the laser light source 15, and allows the fluorescent light from the sample to pass through. Accordingly, in the configuration of the second embodiment, when the laser light source 15 is not turned on and a luminescent pattern is read, the luminescent pattern is read through the dichroic mirror 14, and so although the amount of light that can be detected is reduced, it is otherwise the same as the case of the first embodiment.

The data processor 11 is equipped with the data processing unit 12 which performs a coordinate transformation process and the image memory 13, and when the luminescence pattern is stored in the image memory 13, the data processing unit 12 obtains the scanning position signal from the controller, and from this scanning position signal it converts the polar coordinate system of the positions scanned by the photoreceptor disk into a rectangular coordinate system and stores them in the image memory 13. In this way it is possible to obtain a luminescence pattern no different from that obtained by scanning with a straight-line scanning mechanism.

Figure 7:
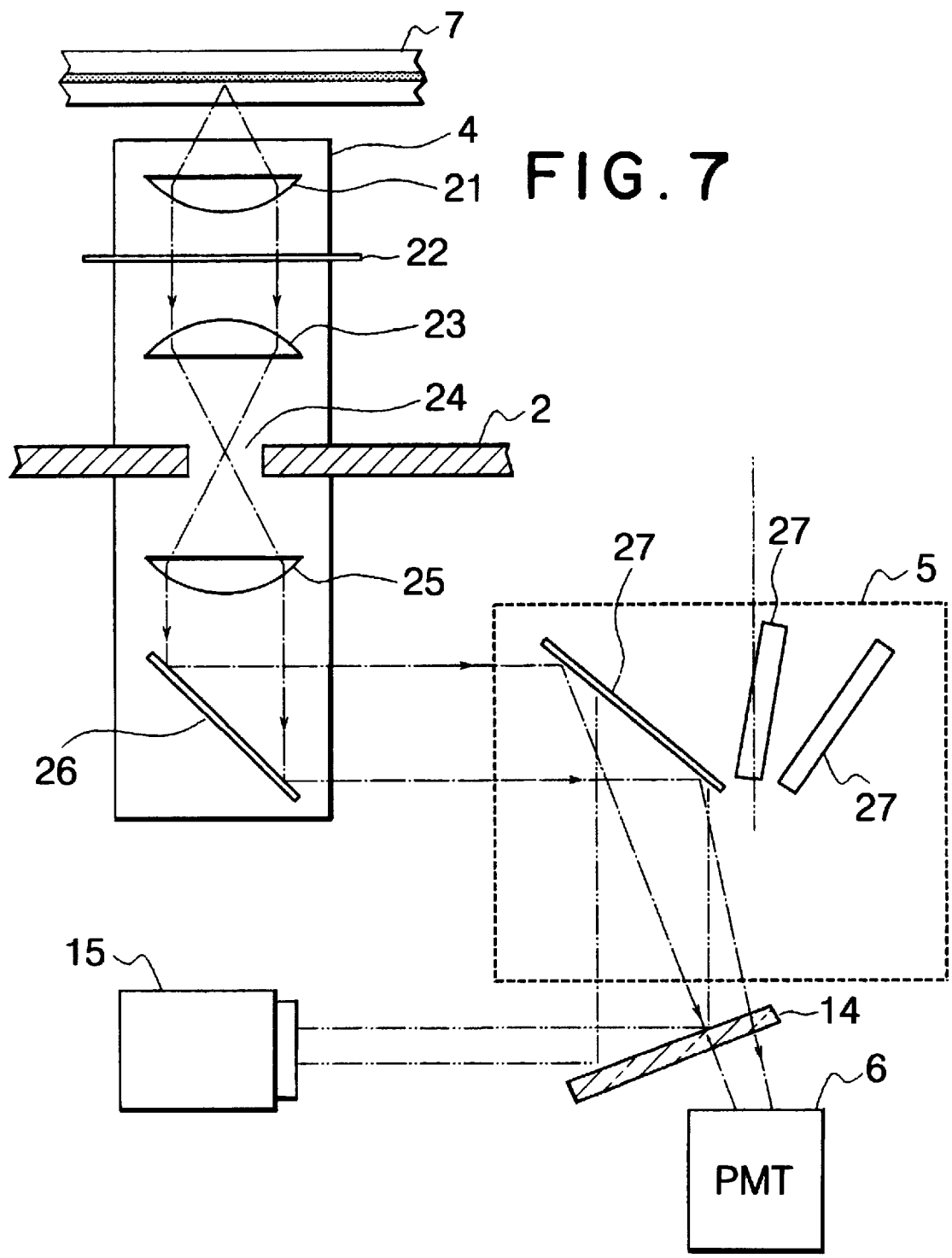
FIG. 7 illustrates the optical path for photoreception of the luminescence pattern with a condenser unit and an optical guide part according to the second embodiment of the present invention.

FIG. 7 illustrates the optical path whereby the luminescence pattern is detected with a condenser unit and an optical guide part according to the second embodiment. In FIG. 7, item 2 is a photoreceptor disk, item 4 is a condenser unit, item 5 is an optical guide part, item 6 is a photomultiplier, item 7 is an electrophoresis gel of the sample to be read, item 14 is a dichroic mirror, item 15 is a laser light source, item 21 is a first lens, item 22 is a wavelength-selective filter, item 23 is a second lens, item 24 is a pinhole, item 25 is a third lens, item 26 is a first planar mirror, and item 27 is a second planar mirror.

The operation is described in the following with reference to FIG. 7. The excitation light source is scanned over and irradiated at the sample by the rotation of the photoreceptor disk 2, and the light of the fluorescent light pattern thereby emitted from the electrophoresis gel 7 of the sample is scanned and read, and stored at a position in the image memory corresponding to this scanning position. This read scanning is also performed by making a plurality of scans over the entire fluorescent light pattern, during which the amounts of light in each pixel of the fluorescent light pattern are accumulated. That is, once a single scan over the entire fluorescent light pattern has been completed, the stage 1 is returned to its starting position, and the read scanning control unit 9 controls the rotary motor 3 and the transport mechanism 8 so as to perform the scan again. These operations are performed repeatedly. As a result, the amounts of light in each pixel of the entire fluorescent light pattern—which is weakly luminescent—are accumulated together, and an image is built up in the pixels corresponding to the fluorescent light pattern.

As shown in FIG. 7, the condenser unit 4 uses a hole part provided in the photoreceptor disk 2 as a pinhole, and is provided with a housing part in which the lenses and the like are provided across both sides of the rotating plate. The lens of the photoreceptor part is installed in the lower part thereof so as to adjoin the electrophoresis gel 7 of the luminescent sample sandwiched between the glass plates. The optical system of the condenser unit 4 consists of a first lens 21, a wavelength-selective filter 22, a second lens 23, a pinhole 24 which is the hole part provided in the rotary disk 2, and a third lens 25, and the optical path of the optical system of optical guide part 5 consists of a first planar mirror 26 and a second planar mirror 27. Also, to shine excitation light onto the electro-phoresis gel 7, it is provided with the laser light source 15 and the dichroic mirror 14, and the dichroic mirror 14 is provided in the optical path between the optical guide part 5 and the photomultiplier 6.

The excitation light from the laser light source 15 is introduced into the optical path via the dichroic mirror 14, and fluorescent light is emitted from the electro-phoresis gel 7 of the sample when this excitation light is irradiated on it. Once this emitted fluorescent light has been collimated by passing through the first lens 21 of the condenser unit 4, the target wavelength is selected by passing through the wavelengths elective filter 22. The light is then condensed by the second lens 23, and the background noise component of the received optical components is eliminated by passing through the pinhole 24, which is the hole part in the photoreceptor disk 2 disposed at the focal point of the second lens 23. That is, the light that has passed through the pinhole 24 corresponds only to the light from a single point on the sample (electrophoresis gel 7). This light is collimated again by the third lens 25 and redirected by the first planar mirror 26 and the second planar mirror 27, and passes through the dichroic mirror 14, whereby its optical path is guided toward the photomultiplier 6, where it is sensed.

Figure 8A:
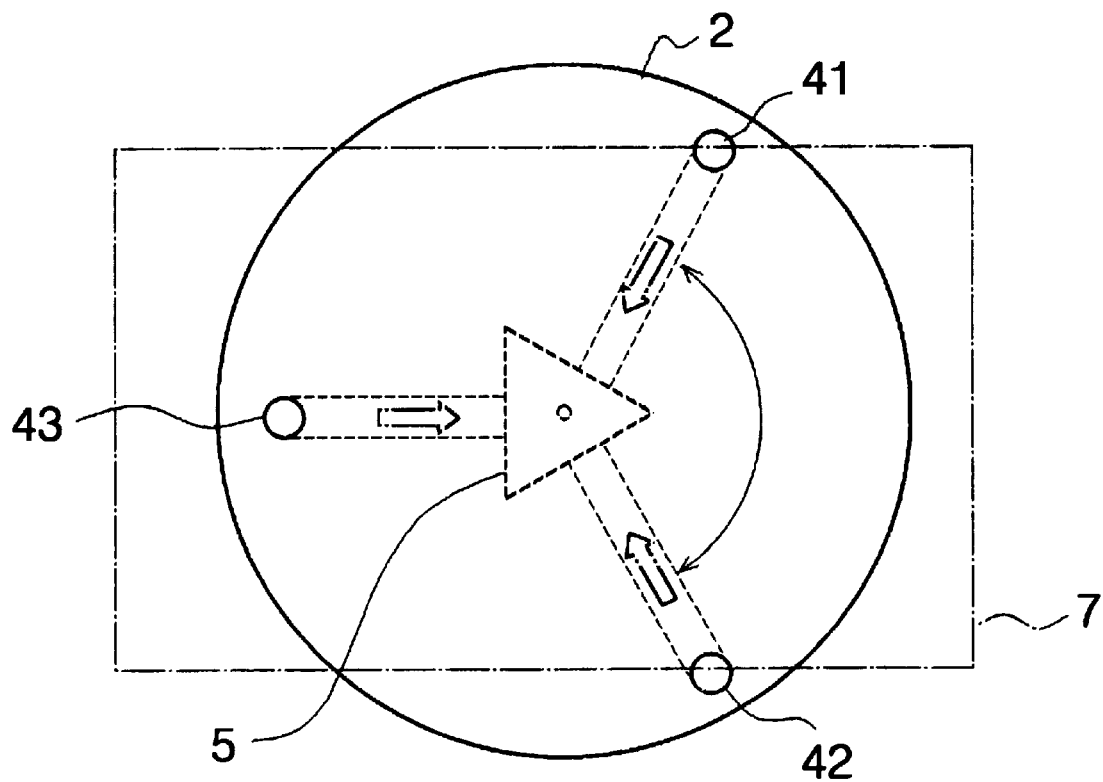
FIGS. 8a and 8b illustrate the positional relationship of the plurality of condenser units provided in a photo-receptor disk configured so as to read a multicolored luminescence pattern in the apparatus for reading a luminescence pattern according to the second embodiment of the present invention.
Figure 8B:
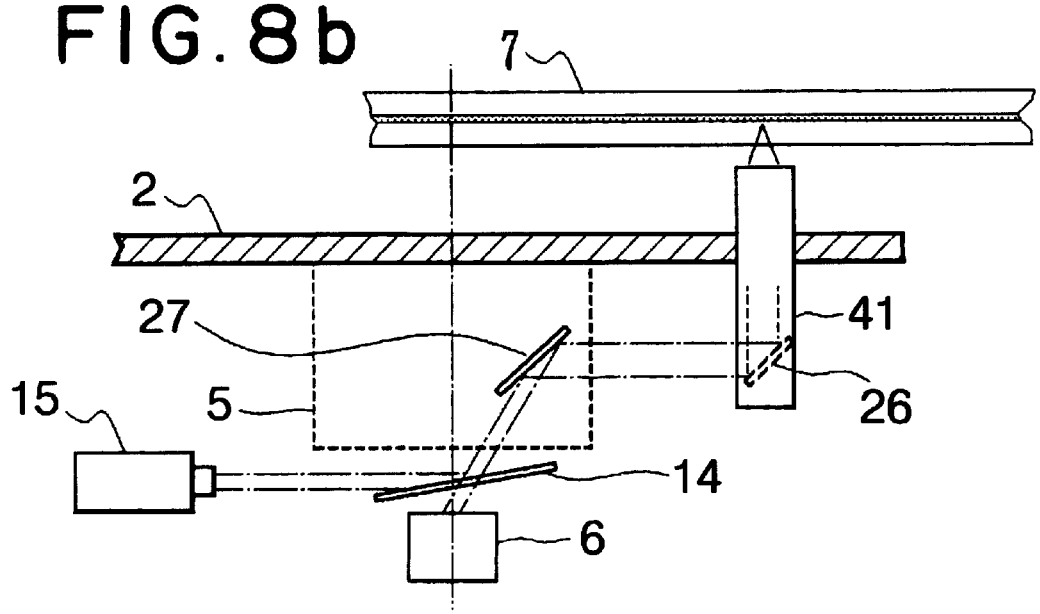

FIGS. 8a and 8b illustrate the positional relationship of the plurality of condenser units provided on a photoreceptor disk configured so as to read a multi-color luminescence pattern in apparatus for reading a luminescence pattern according to the second embodiment; FIG. 8a is a plan view of the photoreceptor disk and FIG. 8b is a side view in partial cross section.

As shown in FIG. 8a, three condenser units 41, 42 and 43 are provided on the photoreceptor disk 2 at positions on the circumference of the same circle and separated from each other by rotational angles of 120 degrees. These three condenser units 41, 42 and 43 each have the same configuration of a pinhole, lenses and the like, but their wavelength-selective filters 22 each have different selection wavelengths, and they are configured to selectively receive light of different colors. In this way, they can scan each color of a multi-color luminescence pattern by condensing light of different colors from the luminescence pattern along the same arc-shaped scan lines.

An optical guide part 5 is provided at the rotational center position of the photoreceptor disk 2, and the light of the luminescence pattern that has been condensed by the lenses and pinholes of each condenser unit 41, 42 and 43 is sent toward the optical guide part 5 provided at the rotational center position of the photoreceptor disk 2 by a planar mirror 26 provided in the lower part of each condenser unit.

As shown in FIG. 8b, the optical guide part 5 is provided with planar mirrors 27 so that it can redirect the light sent in from each of the condenser units 41, 42 and 43 toward the photomultiplier 6, and these planar mirrors 27 are fixed back-to-back opposite each of the condenser units 41, 42 and 43 to form a triangular shape. The optical guide part 5 is fixed to the photoreceptor disk 2 and rotates in unison with the photoreceptor disk 2, and outputs the light from the condenser units 41, 42 and 43 to the photomultiplier 6, which is fixed to the housing of the luminescence pattern reading apparatus (not illustrated) and does not rotate. The photomultiplier 6 is provided at the center of rotation of the photoreceptor disk 2, and its relative positional relationship to the optical guide part 5 does not change. It is noted that a configuration is adopted in which a shutter mechanism (not illustrated) is provided in the optical paths of each of the condenser units, so that when the condenser unit 41 is positioned at the scan line that is currently being read, the light from the condenser units (42 and 43) that are not positioned at a read scanning line does not arrive at the photoreceptor entrance of the photomultiplier 6. Specifically, the shutter mechanism is provided with, for example, a mask that covers two thirds of the optical guide part 5—which rotates in unison with the photoreceptor disk 2—on the left-hand side that is not related to the region over which the reading scan lines move. It is also configured so that the photoreceptor entrance of the photomultiplier 6 is provided slightly shifted from the center of rotation, and so that a mask mechanism or shutter mechanism is provided whereby only light from the condenser unit in the region over which the reading scan lines move is guided to the photoreceptor entrance.

With such a configuration, the gel 7a of the sample is sandwiched between the glass supporting plates 7b and 7c, and fluorescent light from the luminescence pattern of electrophoresis gel 7 of said luminescent sample that is emitted when the excitation light is irradiated on it is condensed at the respective positions of the condenser units 41, 42 and 43 provided on the rotating photoreceptor disk 2 and sent to the optical guide part 5, whereupon, while the photoreceptor disk 2 and the optical guide part 5 rotate, the light from the condenser units 41, 42 and 43 is sent out to the same position at the photoreceptor entrance of the fixed photomultiplier 6 via the fixed dichroic mirror 14. The photomultiplier 6 outputs an electrical signal according to the amount of light condensed from the photoreceptor entrance.

FIG. 9 is a block diagram showing the configuration of the electrical system of the luminescence pattern reading apparatus according to the second embodiment of the present invention. The configuration of the electrical system of the second embodiment is further provided with a light source controller 160 which controls the use of the laser light source according to whether reading is to be performed on a luminescence pattern using the fluorescence method or the chemiluminescence method. That is, as shown in FIG. 9, it comprises a microprocessor (CPU) 150 for executing the control processing of the luminescence pattern reading apparatus, a read-only memory (ROM) 152 for storing the control software program, a random access memory (RAM) 151 which provides a memory area for temporary data storage, an area used for image memory, and a memory area for other forms of data processing, a photoreceptor disk rotation controller 154, a stage transport controller 155, an A/D converter 157 for analog-to-digital conversion of the analog signal made by converting the received light into an electrical signal into digital data, a shading correction circuit 158 for correcting the fixed offset in the optical measurement system of the photoreceptor paths of the condenser units, a light source controller 160 which controls the use of the laser light source according to whether reading is to be performed on a luminescence pattern using the fluorescence method or the chemiluminescence method, and a SCSI controller 153 which controls the interface with an external data processor 159.

The overall electrical system operates as follows: as the power source is connected, each part of the apparatus is first initialized, and when the initialization process has finished, the reading of the sample's luminescence pattern is controlled. Here, details of the initialization process might include processes such as, for example, checking read-only memory (ROM) 152 and random access memory (RAM) 151, checking the rotary operation of the photoreceptor disk, checking the stage transport operation, checking light source controller 160 which turns the laser light source on and off, and initializing the interface unit of the SCSI controller that controls the interface.

On completing the initialization process, the system stands by for a command from the host (data processor 159). When a reading command signal or the like has arrived, this command is processed and it once again returns to the command standby mode. The operations to control the luminescence pattern reading are explained in the description of FIG. 6 above.

Figure 10:
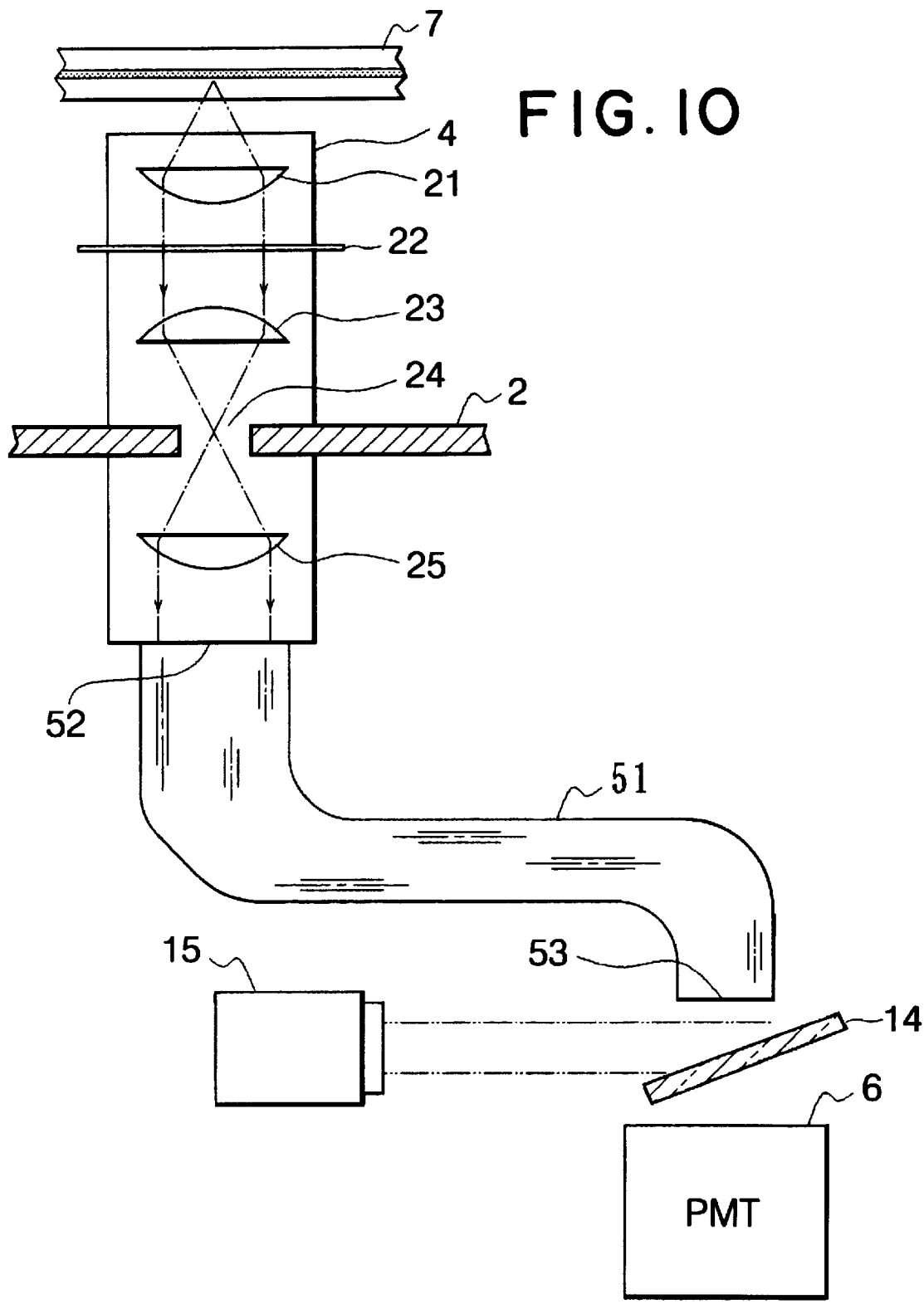
FIG. 10 is a first figure illustrating a variant example in which the optical guide part in the second embodiment of the present invention is configured from an optical fiber.

Next, a variant embodiment of luminescence pattern reading apparatus according to the second embodiment of the present invention is described. FIG. 10 is a first figure illustrating a variant wherein the optical guide part is configured from an optical fiber. The function of the optical guide part is to send light from the condenser unit to the photomultiplier, and so instead of the configuration of two planar mirrors in the abovementioned embodiment it can be configured to use an optical fiber to guide the condensed light directly to the dichroic mirror 14, and after it has passed through the dichroic mirror 14, it is sensed by the photomultiplier 6.

That is, in this variant configuration as shown in FIG. 10, the optical fiber 51 is disposed with its light-entrance end 52 at the light-exiting end from lens 25 of the condenser unit 4, and with its light-exiting end 53 disposed in front of the dichroic mirror 14 so that the light that has passed through the dichroic mirror 14 is introduced into the photoreceptor entrance of the photomultiplier 6. As in the abovementioned embodiment, the optical fiber 51 corresponding to the optical guide part is fixed to the photoreceptor disk 2, and rotates together with photoreceptor disk 2. The light-exiting end of the optical fiber 51 is disposed so as to be positioned on the axis of the photoreceptor disk 2 at the rotational center thereof. The light-exiting ending from the fiber thereby reaches the photoreceptor entrance of the fixed photomultiplier 6.

When this configuration is adapted for multi-color reading, a structure is adopted wherein a plurality of condenser units are provided, and the light-exiting ends of the plurality of optical fibers leading away from these condenser units are brought together so that the light passes through the dichroic mirror 14, and the light that has passed through is gathered together at the position of the photoreceptor entrance of the photomultiplier 6.

Figure 11A:
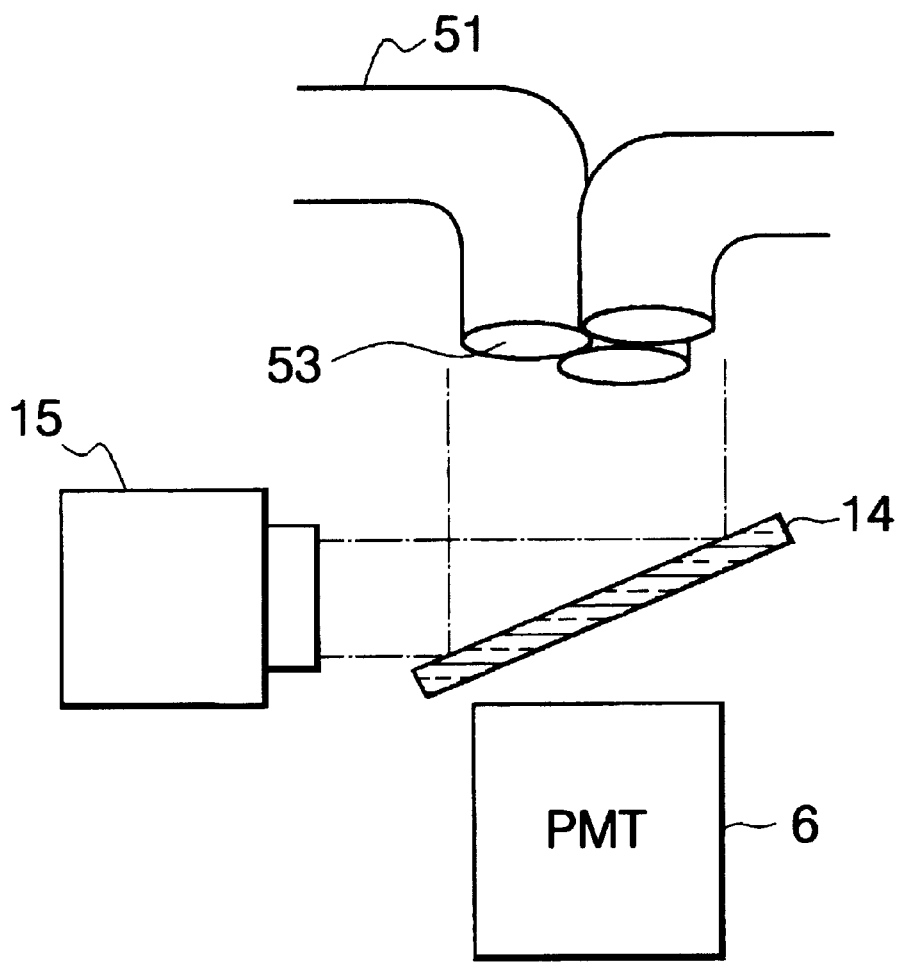
FIGS. 11a and 11b are second and third figures illustrating a variant example in which the optical guide part in the second embodiment of the present invention is configured from an optical fiber.
Figure 11B:
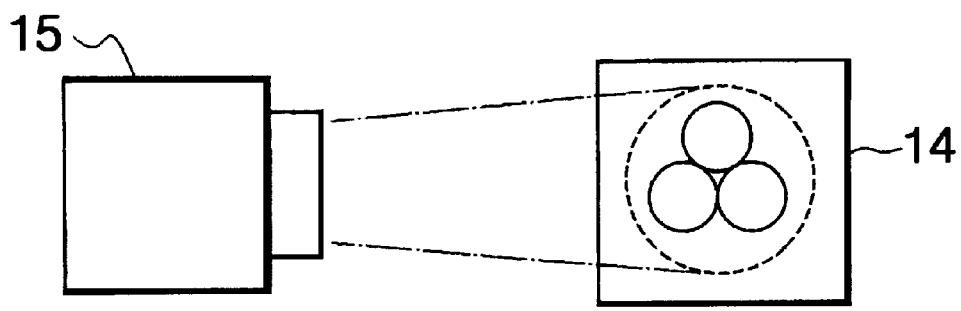

FIGS. 11a and 11b are second and third figures illustrating a second variant wherein the optical guide part is configured from an optical fiber. As shown in FIG. 11a, the light-exiting ends of the optical fibers from a plurality of condenser units adapted for multi-color reading are gathered together and disposed toward the dichroic mirror 14, and the excitation light of broadened width from the laser light source 15 is received from the entire reflecting surface of the dichroic mirror 14. When viewed from below these light-exiting ends, the appearance is as shown in FIG. 11b where, as the light-exiting ends of the plurality of optical fibers rotate, the excitation light of broadened width from the laser light source 15 is introduced, and the fluorescence light from the sample thereby excited is sensed. The sensed fluorescence light passes through the dichroic mirror 14 and is guided into the photoreceptor entrance of the photomultiplier 6.

As described above, with the apparatus for reading a luminescence pattern according to the present invention, when reading a luminescence pattern from a planar sample that emits a faint light, it is possible to use a photosensor to perform the reading at low cost, with high sensitivity and at high speed without using a highly sensitive two-dimensional sensor such as a cooled CCD as has been used hitherto. It is also possible to provide apparatus for reading a fluorescence pattern that is able to read both fluorescent light and chemiluminescent light.

What is claimed is:

1. An apparatus for scanning and reading a luminescence pattern emitted from a sample, comprising:

a stage on which the sample to be read is mounted;

a photoreceptor disk which is rotated so as to scan and condense light from the luminescence pattern of the sample along arc-shaped paths;

a transport mechanism for moving said stage and said photoreceptor disk relative to one another to scan said sample;

an optical guide part for guiding the light from the luminescence pattern, which has been condensed by said photoreceptor disk, to a photoreceptor entrance of a photoelectric converter;

the photoelectric converter receiving the light guided out from said optical guide part, and converting it into an electrical signal;

a controller for controlling the scanning performed by said photoreceptor disk and said transport mechanism, and generating a read scanning position signal; and a data processor for performing data processing by converting the electrical signal from said photoelectric converter into a digital signal, by obtaining a scanning position signal from said controller, and creating an image of the luminescence pattern.

2. The apparatus of claim 1, wherein said data processor is equipped with an image memory for storing the luminescence pattern, and is equipped with a data processing unit for transforming polar coordinates scanned by said photoreceptor disk into rectangular coordinates.

3. The apparatus of claim 1, wherein said photoreceptor disk is equipped with a condenser unit including lenses, a wavelength-selective filter and a pinhole.

4. The apparatus of claim 3, wherein the pinhole of said condenser unit is provided in said photoreceptor disk.

5. The apparatus of claim 1, wherein said optical guide part is an optical fiber whose light-entrance end is connected to the condenser unit of said photoreceptor disk, and whose light-exiting end is provided at a center of rotation of said photoreceptor disk.

6. The apparatus of claim 1, wherein said optical guide part is an optical path whose light-entrance end is a first mirror disposed in the condenser part of said photoreceptor disk, and whose light-exiting end is a second mirror disposed so as to be at a center of rotation of said photoreceptor disk.

7. The apparatus of claim 1, wherein said photoelectric converter is a photomutiplier and is installed at a center of rotation of said photoreceptor disk.

8. The apparatus of claim 1, wherein the condenser unit provided on said photoreceptor disk is provided adjoining said stage.

9. The apparatus of claim 1, wherein said photoreceptor disk is equipped with a plurality of condenser units including lenses, wavelength-selective filters and pinholes, and the wavelength-selective filters of the plurality of condenser units each have different selection wavelengths.

10. An apparatus for scanning and reading a luminescence pattern emitted from a sample, comprising:

a stage on which the sample to be read is mounted;

a photoreceptor disk which is installed in a lower part of said stage and rotates, the photoreceptor disk scanning and condensing light from the luminescence pattern of the sample at positions determined by rotation of said rotary plate;

a transport mechanism for moving said stage and said photoreceptor disk relative to one another to scan said sample;

an optical guide part for guiding the light from the luminescence pattern, which has been condensed by said photoreceptor disk, to a photoreceptor entrance of a photoelectric converter;

a dichroic mirror provided in an optical path of said optical guide part;

an excitation light source for emitting excitation light which is introduced via said dichroic mirror and excites a fluorescent substance in the sample to be read;

a photoelectric converter for receiving the light guided out from said optical guide part, and converting it into an electrical signal;

a controller for controlling the scanning performed by said photoreceptor disk and said transport mechanism, and generating a read scanning position signal; and a data processor for performing data processing by converting the electrical signal from said photoelectric converter into a digital signal, by obtaining a scanning position signal from said controller, and creating an image of the luminescence pattern.

11. The apparatus of claim 10, wherein said data processor is equipped with an image memory for storing the luminescence pattern, and is equipped with a data processing unit for transforming polar coordinates scanned by said photoreceptor disk into rectangular coordinates.

12. The apparatus of claim 10, wherein said photoreceptor disk is equipped with a condenser unit including lenses, a wavelength-selective filter and a pinhole.

13. The apparatus of claim 12, wherein the pinhole of said condenser unit is provided in said photoreceptor disk.

14. The apparatus of claim 10, wherein said optical guide part is an optical fiber whose light-entrance end is connected to the condenser unit of said photoreceptor disk, and whose light-exiting end is provided at a center of rotation of said photoreceptor disk.

15. The apparatus of claim 10, wherein said optical guide part is an optical path whose light-entrance end is a first mirror disposed in the condenser part of said photoreceptor disk, and whose light-exiting end is a second mirror disposed so as to be at a center of rotation of said photoreceptor disk.

16. The apparatus of claim 10, wherein said photoelectric converter is a photomutiplier and is installed at a center of rotation of said photoreceptor disk.

17. The apparatus of claim 10, wherein the condenser unit provided on said photoreceptor disk is provided adjoining said stage.

18. The apparatus of claim 10, wherein said photoreceptor disk is equipped with a plurality of condenser units including lenses, wavelength-selective filters and pinholes, and the wavelength-selective filters of the plurality of condenser units each have different selection wavelengths.

19. The apparatus of claim 10, wherein the dichroic mirror is provided at the light-exiting end of said optical guide part and at the center of rotation of said photoreceptor disk, and wherein the excitation light of said excitation light source is produced using a laser light source with expanded beam width.

20. The apparatus of claim 10, wherein said photoreceptor disk is equipped with a plurality of condenser units including lenses, wavelength-selective filters and pinholes, and the wavelength-selective filters of the plurality of condenser units each have different selection wavelengths, the dichroic mirror is provided at a light-exiting end of said optical guide part and at a center of rotation of said photoreceptor disk, and the excitation light of said excitation light source is produced using a laser light source with expanded beam width in a range in which the sample to be scanned is read with respect to the dichroic mirror.

21. The apparatus according to claim 10, wherein the excitation light source is a laser.

22. The apparatus of claim 10, wherein said optical guide part includes an optical fiber.

23. The apparatus of claim 10, wherein said optical guide part includes a plurality optical fibers.

24. An apparatus for scanning a luminescence pattern of a sample comprising:

a stage onto which the sample in mounted;

a photoreceptor disk which is rotated so as to scan the sample on the stage along an arc-shaped path, wherein light emitted from the luminescence pattern is condensed by the photoreceptor disk; and a transport mechanism for moving the stage relative to the photoreceptor disk so that the sample can be scanned by a plurality of arc-shaped paths.

25. The apparatus according to claim 24, further comprising an excitation light source for exciting a fluorescent substance in the sample.

26. The apparatus according to claim 25, wherein the excitation light source is a laser.

27. The apparatus according to claim 24, further comprising means for processing the light condensed by the photoreceptor disk to create an image of the luminescence pattern.

* * * * *